United States Patent [19]

Toyoshi et al.

[11] Patent Number: 4,523,999

[45] Date of Patent: Jun. 18, 1985

[54] ULTRAFILTRATION METHOD

[75] Inventors: Seiji Toyoshi; Tetsuo Tanegawa, both of Saga; Masaru Saeki, Fujisawa; Tetsuya Kawakita, Yokohama, all of Japan

[73] Assignee: Ajinomoto Co., Inc., Tokyo, Japan

[21] Appl. No.: 561,974

[22] Filed: Dec. 16, 1983

[51] Int. Cl.$^3$ .............................................. B01D 13/00
[52] U.S. Cl. .................................... 210/639; 127/48; 127/55; 210/651; 435/110; 435/115
[58] Field of Search ...................... 127/48, 51, 54, 55; 210/638, 639, 650, 651, 702, 724; 435/106, 110-112, 115, 276

[56] References Cited

U.S. PATENT DOCUMENTS

| | | | |
|---|---|---|---|
| 3,799,806 | 3/1974 | Madsen | 210/639 |
| 3,986,933 | 10/1976 | Maldonado et al. | 435/110 |
| 4,069,103 | 1/1978 | Muller | 127/54 |
| 4,278,766 | 7/1981 | Srinivasan | 435/110 |
| 4,411,991 | 10/1983 | Hirakawa et al. | 426/43 |
| 4,416,700 | 11/1983 | Clark et al. | 210/639 |

FOREIGN PATENT DOCUMENTS

| | | | |
|---|---|---|---|
| 937058 | 9/1963 | United Kingdom . | |
| 973828 | 10/1964 | United Kingdom | 435/110 |
| 1015637 | 1/1966 | United Kingdom . | |
| 2113247 | 8/1983 | United Kingdom | 127/55 |

OTHER PUBLICATIONS

Michaels, "New Separation Technique for the CPI", Chem. Eng. Progress, Dec. 1968, pp. 31–43.

Primary Examiner—Peter Hruskoci
Attorney, Agent, or Firm—Oblon, Fisher, Spivak, McClelland & Maier

[57] ABSTRACT

A method for removing impurities including humic substances, gums, polysaccharides, proteins or a mixture thereof from an amino acid fermented liquor obtained from cane, beet molasses, or a mixture thereof, said amino acid being selected from the group consisting of glutamic acid, lysine, and a mixture thereof; said method comprising:

(a) adjusting the pH of the fermented liquor to a value of from 2–5 to precipitate said impurities, said impurities having an isoelectric point falling within a pH range of 2–5;

(b) ultrafiltering said impurities from said fermented liquor using a semipermeable ultrafiltration membrane.

9 Claims, No Drawings

ULTRAFILTRATION METHOD

DETAILED DESCRIPTION OF THE INVENTION

The present invention is, on removing polymer impurities such as humic substances, dyes etc. contained in an amino acid fermented liquor or its intermediate treated liquor before the intended amino acid is separated and obtained therefrom, to aggregate the aforesaid impurities by previously adjusting the pH of the liquor to a specified value, thus enhancing the degree of blocking thereof. More specifically, in a system containing polymer impurities, e.g. a fermented liquor starting from cane or beet molasses or its intermediate treated liquor, the kinds of said impurities are varied, for example, dyes, humic substances, gums, polysaccharides, proteins etc. Among those, the humic substances and certain dyes are the so-called acidic substances having a carboxyl group as a functional group, and in a certain acidic region, they become a non-charged state and lose affinity with water, thus resulting in precipitation. The object of the present invention is to aggregate and precipitate these polymer substances by adjusting the pH of such a fermented liquor or its intermediate treated liquor to a specific acidic region by utilizing the aforesaid property, thereby increasing the degree of blocking in the ultrafiltration treating operation.

The certain acidic region as herein used is pH 2-5. This region is suitable because the isoelectric points of the certain dyes and humic substances fall within it or its vicinity. However, if the isoelectric point of the intended amino acid falls within this region, it is a matter of course to exclude said isoelectric point and its neighboring region. Adjustment of pH may be satisfactorily achieved by using acid or alkali, and examples of the acid which may be employed are the so-called mineral acids such as hydrochloric acid, sulfuric acid, nitric acid, phosphoric acid etc. and organic acids such as acetic acid etc., while as the alkali, there are sodium hydroxide, potassium hydroxide, lime, ammonia etc.

Practical points of operations of the present invention are now described.

The liquor to be treated by the present invention is an amino acid fermented liquor employing as a carbon source cane or beet molasses or its intermediate treated liquor as described above, and before subjecting this liquor to the ultrafiltration treatment, the pH thereof is previously adjusted to 2-5 (except the isoelectric point of the intended amino acid and its vicinity).

The thus pH-adjusted liquor is subjected to the ultrafiltration treatment, and the ultrafiltration treatment per se may be a conventional known method. For example, the material for the membrane employed in the filtration may be a conventional semipermeable membrane and there is no particular restriction thereon. For example, polyamide, polyacrylonitrile, cellulose acetate type etc. may be contemplated. The shape of the membrane is also not restricted and may be for example, a tubular, flat film, spiral, hollow fiber membrane etc. The conditions, e.g. temperature etc. are also nothing particular.

The effect of the present invention is demonstrated by the following examples. In the examples, the percent of dyes excluded was measured by the absorbance at 400 nm and the percent of polymers removed was by the Lowly Folin method utilizing the reducing property of humic substances.

EXAMPLE 1

A glutamic acid fermented liquor (pH 7.2) starting from cane molasses was adjusted to pH 4.8 with hydrochloric acid, then subjected to ultrafiltration treatment employing a polyacrylonitrile hollow fiber-shaped ultrafiltration membrane (molecule fraction 13,000) at 40° C., and compared with the case where the fermented liquor (pH 7.2) was directly treated by ultrafiltration.

The results are shown in Table 1.

TABLE 1

|  |  | Percent of Polymers Removed | Percent of Dyes Excluded |
|---|---|---|---|
| (Control) | Glutamic Acid Fermented Liquor (pH 7.2) | 10 (%) | 20 (%) |
| (Present Invention) | Above Fermented Liquor Adjusted to pH 4.8 | 15 | 30 |

From the above table, it can be understood that by adjusting the pH to a predetermined value, the percent of the polymeric reducing substances removed has been increased by 50% and the percent of the dyes excluded by 50%.

EXAMPLE 2

A lysine fermented liquor starting from cane molasses (pH 7.2) per se (Control) and that further adjusted to pH 4 (Present Invention) were subjected to ultrafiltration similarly as in Example 1.

The results are shown in Table 2. From this table, it can be seen that by the present invention, the percent of the polymeric reducing substances removed has been increased by 36% and the percent of the dyes excluded by 60%.

TABLE 2

|  |  | Percent of Polymers Removed | Percent of Dyes Excluded |
|---|---|---|---|
| (Control) | Lysine Fermented Liquor (pH 7.0) | 14 (%) | 15 (%) |
| (Present Invention) | Above Fermented Liquor Adjusted to pH 4 | 19 | 24 |

EXAMPLE 3

A lysine fermented liquor (pH 7.0) starting from beet molasses was adjusted to pH 3.0 with sulfuric acid, then subjected to ultrafiltration treatment employing a polyacrylonitrile hollow fiber-shaped ultrafiltration membrane (molecule fraction 6,000) at 50° C., and compared with the case where the fermented liquor (pH 7.0) was directly treated by ultrafiltration.

The results are shown in Table 3.

TABLE 3

|  |  | Percent of Polymers Removed | Percent of Dyes Excluded |
|---|---|---|---|
| (Control) | Lysine Fermented Liquor (pH 7.0) | 30 (%) | 37 (%) |
| (Present Invention) | Above Fermented Liquor Adjusted to pH 3 | 50 | 63 |

From the above table, it can be understood that the percent of the polymeric reducing substances removed has been increased by 67% and the percent of the dyes excluded by 70% in accordance with this invention.

What is claimed is:

1. A method for removing impurities including humic substances, gums, polysaccharides, proteins or a mixture thereof from an amino acid fermented liquor obtained from cane, beet molasses, or a mixture thereof, said amino acid being selected from the group consisting of glutamic acid, lysine and a mixture thereof; said method comprising:
   (a) adjusting the pH of the fermented liquor to a value of from 2–5 to precipitate said impurities, said impurities having an isoelectric point falling within a pH range of 2–5;
   (b) ultrafiltering said impurities from said fermented liquor using a semipermeable ultrafiltration membrane.

2. The method of claim 1 wherein said amino acid fermented liquor comprises an intermediate liquor obtained from cane molasses, beet molasses or a mixture thereof.

3. The method of claim 1 wherein said pH is adjusted by adding an acid or an alkali to the amino acid fermented liquor.

4. The method of claim 3 wherein said acid comprises a mineral acid, an organic acid, or a mixture thereof.

5. The method of claim 4 wherein said mineral acid comprises hydrochloric acid, sulfuric acid, nitric acid, phosphoric acid, or a mixture thereof.

6. The method of claim 4 wherein said organic acid comprises acetic acid.

7. The method of claim 3 wherein said alkali comprises sodium hydroxide, potassium hydroxide, lime, ammonia, or a mixture thereof.

8. The method of claim 1 wherein said semipermeable membrane is made up of polyamide, polyacrylonitrile, cellulose acetate, or a mixture thereof.

9. The method of claim 1 wherein said membrane has a tubular, flat film, spiral, or hollow fiber membrane shape.

* * * * *